United States Patent
Varadaraj

(10) Patent No.: US 8,980,618 B2
(45) Date of Patent: Mar. 17, 2015

(54) ALGAE AGGREGATION AND HARVESTING

(71) Applicant: Ramesh Varadaraj, Bartlesville, OK (US)

(72) Inventor: Ramesh Varadaraj, Bartlesville, OK (US)

(73) Assignee: Exxonmobil Research and Engineering Company, Annandale, NJ (US)

(*) Notice: Subject to any disclaimer, the term of this patent is extended or adjusted under 35 U.S.C. 154(b) by 0 days.

(21) Appl. No.: 14/055,123

(22) Filed: Oct. 16, 2013

(65) Prior Publication Data

US 2014/0141496 A1 May 22, 2014

Related U.S. Application Data

(60) Provisional application No. 61/727,835, filed on Nov. 19, 2012.

(51) Int. Cl.
*C12N 1/12* (2006.01)

(52) U.S. Cl.
CPC ........................................ *C12N 1/12* (2013.01)
USPC ...................................................... 435/257.1

(58) Field of Classification Search
CPC ........................................................ C12N 1/12
USPC ...................................................... 435/257.1
See application file for complete search history.

(56) References Cited

U.S. PATENT DOCUMENTS

2010/0184197 A1* 7/2010 Dong et al. ................ 435/257.1

OTHER PUBLICATIONS

Pan "Dewatering characteristics of algae-containing alum sludge" Colloids and Surfaces A: Physiochemical and Engineering Aspects, 150 (1999) 185-190).*
Lavoie "Harvesting of Scendesmus obliquus in Wastewaters: Auto- or Bioflooculation" Biotechnology and Bioengineering vol. 30, 852-859 (1987).*
Mohan, J., Rao, R, Kumar, R., Sivasankaran, S., Sivasubramanian, V., "Studies on Mass Cultivation of *Chlorella vulgaris* and Effective Harvesting of Bio-Mass by Low-Cost Methods", Journal of Algal Biomass Utilization, 2009, pp. 29-39, vol. 1(1), Phyco Spectrum Inc.
Brink, J., "The cultivation and harvesting of micro-algal biomass", Dissertation Abstracts International, 2011, p. 62, p. 99 (fig. 46), p. 140, Chemical Engineering the Potchefstroom campus of the North-West University.
Piccolo, A., "Aquatic Biofeuls: New Options for Bioenergy", Dissertation Abstracts International, 2009, p. 12, Link Campus—University of Malta.

* cited by examiner

*Primary Examiner* — Jon P Weber
*Assistant Examiner* — Charles Zoltan Constantine
(74) *Attorney, Agent, or Firm* — David M. Weisberg

(57) ABSTRACT

Methods are provided for separating algae from an aqueous environment. An aqueous feed containing algae can be aged for a period of at least about 90 hours without purging or other aeration. The aging of the aqueous feed can result in formation of aggregated algae, which can then be filtered under pressure. Due to the larger size of the algae aggregates, the pressurized filtration can reduce/minimize the tendency to clog the filter, as the algae aggregates can generally be too large to fit within the pores of the filter. The filter can preferably be located at the bottom of the vessel holding the aqueous feed. This can assist in allowing the algae to remain in a cake above the filter, as opposed to having the algae dissolve back into the aqueous feed.

20 Claims, 1 Drawing Sheet

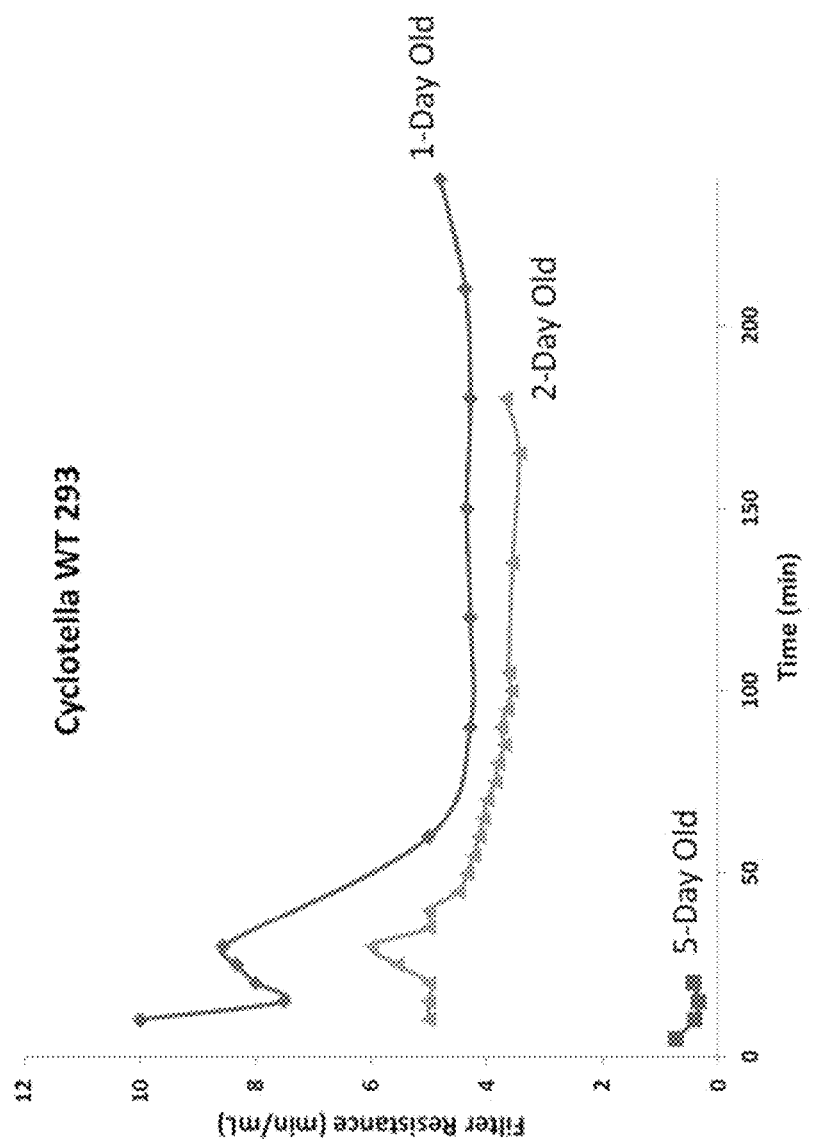

ALGAE AGGREGATION AND HARVESTING

CROSS-REFERENCE TO RELATED APPLICATIONS

This application claims the benefit of U.S. Provisional Application Ser. No. 61/727,835 filed on Nov. 19, 2012; which is incorporated herein in its entirety by reference.

FIELD OF THE INVENTION

This invention relates to methods for harvesting algae from an aqueous environment.

BACKGROUND OF THE INVENTION

Developing renewable sources of feedstocks based on biomass for making distillate products, such as fuels or lubricants, is an area of ongoing interest. Use of biomass as a feedstock source can be attractive from a perspective of avoiding depletion of mineral oil and gas sources. However, a variety of challenges remain in developing technologies for harvesting and processing feeds derived from biomass.

One potential source of biomass-derived feedstocks is algae. Algae is an advantageous form of biomass in part because algae can be grown in artificially constructed ponds. Such algae growth ponds can be placed in desirable locations, such as locations that do not compete with production of food for human consumption. However, algae grown in a pond or other aqueous environment are typically present in a concentration corresponding to a few weight percent of the environment or less. Thus, one of the difficulties with using algae as a biomass source is the need to separate the relatively low concentration of algae from the water which is the majority component of the aqueous environment.

Some previous efforts to separate algae from an aqueous environment have used dissolved air flotation. In a conventional dissolved air flotation method, air is bubbled into an aqueous environment containing algae. The air is bubbled into the aqueous environment with the goal of having the algae attach to or agglomerate on the bubbles. As the bubbles reach the surface of the aqueous environment, algae becomes concentrated at the surface. The surface of the aqueous environment can then be skimmed to capture the algae at the surface. However, the skimming process tends to be inefficient, in part because algae that have traveled to the surface of the aqueous environment can fall back into the bulk portion of the environment. The algae that remain in the aqueous environment pose problems in part due to environmental regulations for the allowable concentration of species in waste water. Additionally, controlling the conditions in the aqueous environment is difficult, as the process is sensitive to small fluctuations within the environment.

SUMMARY OF THE INVENTION

In an embodiment, a method is provided for harvesting algae. The method includes aging an aqueous feed containing algae in an unaerated environment for a period of at least about 90 hours; and filtering the aqueous feed through a filter medium at a pressure of about 25 psig (about 170 kPag) to about 1500 psig (about 10.3 MPag) to substantially separate the algae from the aqueous feed.

In another embodiment, a method is provided for harvesting algae. The method includes aging an aqueous feed containing at least two types of algae in an unaerated environment for a period of at least about 90 hours, the algae comprising at least 10 wt % of each of the at least two types of algae relative to the total weight of algae in the feed; and filtering the aqueous feed through a filter medium at a pressure of about 25 psig (about 170 kPag) to about 1500 psig (about 10.3 MPag) to substantially separate the algae from the aqueous feed.

In still another embodiment, a method is provided for harvesting algae, comprising: aging an aqueous feed containing algae in an unaerated environment for a period of at least about 90 hours, the algae comprising at least 10 wt % of a first type of algae relative to the total weight of algae in the feed, and at least 10 wt % of a second type of algae relative to the total weight of algae in the feed, the first type of algae having a first morphology and the second type of algae having a second morphology; and filtering the aqueous feed through a filter medium at a pressure of about 25 psig (about 170 kPag) to about 1500 psig (about 10.3 MPag) to substantially separate the algae from the aqueous feed.

BRIEF DESCRIPTION OF THE DRAWINGS

FIG. 1 shows filtration rates for algae cultures after various amounts of aging.

DETAILED DESCRIPTION OF THE EMBODIMENTS

In various embodiments, methods are provided for separating algae from an aqueous environment. An aqueous feed containing algae can advantageously be aged for a period of at least about 90 hours. Preferably, the aqueous feed can be aged in a closed vessel, so that any gases in the closed vessel can substantially not be exchanged with the environment outside of the vessel. Preferably, the aqueous feed can be aged without purging. The aging of the aqueous feed can result in formation of a crystalline or quasi-crystalline algae phase comprising aggregated algae. The aqueous feed can then be filtered under pressure. Due to the larger size of the crystallized or quasi-crystallized algae aggregates, the pressurized filtration can reduce/minimize a tendency to clog the filter, as the algae aggregates can generally be too large to fit within the pores of the filter. The filter can preferably be located at the bottom of the vessel holding the aqueous feed. This can assist in allowing the algae to remain in a cake above the filter, as opposed to having the algae dissolve back into the aqueous feed.

Algae Feedstock

In the discussion herein, a feed derived from a biological source (i.e., a biocomponent feed(stock)) refers to a feedstock derived from a biological raw material component, such as vegetable fats/oils or animal fats/oils, fish oils, pyrolysis oils, and algae lipids/oils, as well as components of such materials. In particular, a feed derived from a biological source can be a feed of algae in an aqueous environment, such as an algae culture or other feed containing algae in water.

Major classes of lipids can include, but are not necessarily limited to, fatty acids, glycerol-derived lipids (including fats, oils and phospholipids), sphingosine-derived lipids (including ceramides, cerebrosides, gangliosides, and sphingomyelins), steroids and their derivatives, terpenes and their derivatives, fat-soluble vitamins, certain aromatic compounds, and long-chain alcohols and waxes.

In living organisms, lipids generally serve as the basis for cell membranes and as a form of fuel storage. Lipids can also be found conjugated with proteins or carbohydrates, such as in the form of lipoproteins and lipopolysaccharides.

Algae oils or lipids can typically be contained in algae in the form of membrane components, storage products, and/or metabolites. Certain algal strains, particularly microalgae such as diatoms and cyanobacteria, can contain proportionally high levels of lipids. Algal sources for the algae oils can contain varying amounts, e.g., from 2 wt % to 40 wt %, of lipids based on total weight of the biomass itself Algal sources for algae oils can include, but are not limited to, unicellular and multicellular algae. Examples of such algae can include a rhodophyte, chlorophyte, heterokontophyte, tribophyte, glaucophyte, chlorarachniophyte, euglenoid, haptophyte, cryptomonad, dinoflagellum, phytoplankton, and the like, and combinations thereof. In one embodiment, algae can be of the classes Chlorophyceae and/or Haptophyta. Specific species can include, but are not limited to, *Neochloris oleoabundans, Scenedesmus dimorphus, Euglena gracilis, Phaeodactylum tricornutum, Pleurochrysis carterae, Prymnesium parvum, Tetraselmis chui,* and *Chlamydomonas reinhardtii*. Additional or alternate algal sources can include one or more microalgae of the *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Cryptheocodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Pichochlorum, Pseudoneochloris, Pseudostaurastrum, Platymonas, Pleurochrysis, Pleurococcus, Prototheca, Pseudochlorella, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella,* and *Volvox* species, and/or one or more cyanobacteria of the *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Tolypothrix, Trichodesmium, Tychonema,* and *Xenococcus* species.

Aging of an Algae Feed or Sample

Aging can be performed by maintaining an algae feed in a closed vessel without purging. Preferably, the vessel can be closed (not open to the environment), so that exchange of gases with the ambient environment surrounding the vessel can be reduced or even eliminated. The aging can also be performed without agitation of the closed vessel. Optionally, the closed vessel can also be opaque relative to visible and/or ultraviolet wavelengths, so that the algae feed within the closed vessel need not be exposed to light.

The temperature of the algae feed during aging can be approximately ambient or room temperature, such as from about 10° C. to about 40° C. Cooler temperatures still above the freezing point of water could also be acceptable, but may not be preferred. Temperatures of about 35° C. to about 40° C. can also be acceptable, but these temperatures and higher may be detrimental to the crystallization process. The pressure during aging can be any convenient pressure, such as ambient pressure.

Preferably, the aging can be performed for at least about 90 hours, e.g., at least about 120 hours or at least about 150 hours. During aging, the algae can excrete at least one compound. One or more of the excreted compounds can then assist or facilitate the algae in forming a crystalline or quasi-crystalline structure of aggregated algae. The at least one excreted compound can correspond to a compound (or compounds) that are excreted by the algae when the algae are in an environment that is deficient in at least one nutrient. The deficient nutrient can be a nutrient present in an amount below a threshold level for algae growth, or the deficient nutrient can be entirely missing. The deficient nutrient can be a gas nutrient, such as air ($O_2$) or $CO_2$; a nutrient within the aqueous algae feed, such as nitrogen or phosphorous; light energy; or another nutrient; or a combination thereof Aggregation of the algae can result in an increase in the average effective "particle size" of the algae. Instead of the algae behaving like individual particles, aggregation can cause the algae to behave according to the larger size of the aggregated algae. Individual algae can have a variety of sizes, depending on the type of algae. The size of individual algae can range from about 0.5 µm to about 10 µm. By forming algae aggregates, the characteristic size for algae can be increased. The increased aggregate size of the algae aggregates can reduce the tendency of the algae to clog the pores of the filter medium. Similarly, the larger aggregate size can also reduce the tendency of the algae to form a filter cake with a low permeability. In some embodiments, algae aggregates can have a characteristic size of at least about 15 µm and less than about 200 µm.

Forming aggregated algae crystals and/or quasi-crystals can reduce/minimize the amount of clogging of pores that occurs during filtration. During a conventional filtration process for an algae feed, the channels or pores in the filter medium can tend to clog. This can be due in part to the individual algae cells becoming stuck in the pores of the filter medium.

The increased size of the algae aggregates can also improve filtration rates based on avoiding formation of a filter cake on the surface of the filtration medium that can have a low permeability for water. The packing density for particles with a regular shape can typically be invariant with the radius (or other characteristic length) for the particles. For example, the density of hard spherical particles can depend on the type of packing arrangement, but the density may be independent of the radius of the spheres, so long as all of the spheres have the same size. However, the way the volume between particles is distributed can generally vary with size. For a close packed arrangement of spheres, the size of the gaps or channels between the spheres can typically increase as the radius of the spheres increases.

During filtration of algae from an aqueous environment, the algae can tend to accumulate in a filter cake on the retentate side of the filter medium. During filtration, the material that accumulates in the filter cake can add to the pressure drop required to pass liquid through the filter. For particles with larger particle sizes, the gaps or channels in the filter cake can be larger, which can reduce the pressure drop required to pass liquid through the filter cake. By forming algae aggregates, the average "particle" size in the algae feed can be increased from the algae size to the algae aggregate size. Based on this increase in effective particle size, formation of algae aggregates can reduce the pressure drop required to pass water through the filter cake during filtration.

In addition to increasing the average particle size, forming algae aggregates can also change the morphology of the "particles" in the algae feed. For example, individual algae can have various shapes, such as spherical, cylindrical, disc-like, or irregular. When the individual algae are aggregated, however, the shape of the aggregated algae may not match the morphology of the individual algae. The shape and size of the aggregates formed from algae can be dependent on the nature of the algae, including the surface properties (such as roughness) for the algae. For example, an algae type with individual algae of a spherical morphology may form aggregates of an irregular shape. Any type of irregular shape can have a reduced packing density that may improve the flow properties through a filter cake formed during filtration.

Still another option for improving the flow properties through a filter cake can be to use an algae feed with more than one type of algae. Having multiple types of algae, such as at least two types of algae, can provide a filter cake with improved filtration properties for a variety of reasons. First, for particles of different shapes, the presence of multiple shapes can tend to reduce the potential packing density. Preferably, the characteristic lengths of the algae can be sufficiently similar so that the algae with smaller characteristic lengths do not occupy void spaces within an aggregate of the algae with larger characteristic lengths.

One option can be to use a mixture of algae types, such as at least two types of algae, so that a first type of algae with beneficial properties for aggregation and/or packing density can be combined with a second type of algae with other desirable properties but poor aggregation and/or poor properties in a filter cake. For example, an algae with good aggregation properties can be mixed with an algae that is efficient for production of desirable product molecules. In some embodiments, an algae with good aggregation properties can include an algae that excretes one or more compounds beneficial for forming crystalline or quasi-crystalline aggregates.

In various aspects, algae feeds containing more than one type of algae can comprise at least 10 wt % of a first type (such as species or strain) of algae, relative to the total weight of algae in the feed, and at least 10 wt % of a second type of algae. Due to the relatively low concentration of algae in many algae feeds, it is noted that the total weight percent of all algae in a feed can typically be less than 10 wt % relative to the weight of the feed. In one embodiment, the weight percentage of the first type of algae can be greater than the second type of algae. The ratio of the first type of algae to the second type of algae can be at least 1:1, e.g., at least 1.5:1, at least 2:1, or at least 3:1. Additionally or alternatively, the ratio of the first type of algae to the second type of algae can be 9:1 or less, e.g., 6:1 or less, 5:1 or less, or 4:1 or less.

In still other aspects, more than two types of algae may be included in the algae feed. In general, an algae feed can contain any number of algae types. However, algae types that are present as less than about 10 wt % of the total algae content are not believed to have a substantial impact on the resulting aggregate structures. Of course, a blend of various types of algae can also be viewed as a single "mixed" type of algae for the purposes of characterizing the performance of the feed during filtration.

When an algae feed contains a mixture of two or more types of algae, the morphology of each type of algae can be any convenient morphology. Examples of morphology for algae include spherical, cylindrical, disc-like, and irregular. It is noted that a spherical morphology, for example, may not be perfectly spherical and may be only approximately spherical. Preferably, at least two of the algae types in the mixture can have different morphologies. For spherical or disc-like morphology, a characteristic dimension for an algae can be a diameter. For a cylindrical morphology, a characteristic dimension for an algae can be a length. Preferably, a ratio of characteristic dimensions for a first type of algae and a second type of algae can be from about 1:3 to about 3:1, e.g., less than 2:1 and/or at least 1:2.

Filtration of Aqueous Feed Containing Aggregated Algae

Filtration of the aqueous feed to separate the aggregated algae from water can be performed after aging to allow for algae aggregation. During filtration, the temperature can be maintained near ambient temperature, such as from about 10° C. to about 40° C. The pressure during filtration can be a pressure that facilitates transporting water through the filter medium. The pressure can preferably be selected to provide a sufficient pressure differential for filtration at a commercially desirable speed. Depending on the embodiment, pressures from about 25 psig (about 170 kPag) to about 1500 psig (about 10.3 MPag) can be suitable, e.g., at least about 40 psig (about 280 kPag), at least about 100 psig (about 690 kPag), about 1000 psig (about 6.9 MPag) or less, and/or about 600 psig (about 4.1 MPag) or less.

During filtration, the algae feed can be filtered through the filter medium in a direction roughly aligned with gravity, such as a direction that differs from the direction of gravitational pull by ~45° or less. This can reduce/minimize the tendency for the algae in the filter cake to re-enter the aqueous feed on the retentate side.

The filter medium can be any convenient type of membrane, filter, or other porous material suitable for performing filtration. The pore size of the filter medium can be about 20 μm or less, e.g., about 10 μm or less, about 5 μm or less, or about 3 μm or less. Preferably, the pore size of the filter medium can be at least about 1 μm in order to facilitate appropriately high filtration rates.

More generally, selection of a suitable filter medium with a suitable pore size can be made depending on the individual algae size and the size of the aggregates. The aggregate size can be determined by optical microscopy techniques well known in the art of sizing particles. Additionally or alternately, the aggregate size can be determined using techniques like laser reflectance microscopy.

Using filtration to separate algae from the aqueous environment as filtration can be a reliable method for reducing the algae content of the permeate to a sufficiently low level to meet typical standards for purified wastewater. As a result, the need for further processing of the permeate water prior to disposal can be reduced, minimized, or eliminated.

Additional Embodiments

Embodiment 1. A method for harvesting algae, comprising: aging an aqueous feed containing algae in an unaerated environment for a period of at least about 90 hours; and filtering the aqueous feed through a filter medium at a pressure of about 25 psig (about 170 kPag) to about 1500 psig (about 10.3 MPag) to substantially separate the algae from the aqueous feed.

Embodiment 2. The method of Embodiment 1, wherein the algae separated from the aqueous feed comprise algae aggregates.

Embodiment 3. The method of Embodiment 2, wherein the algae have a characteristic size of about 10 μm or less and the algae aggregates have a characteristic size of at least about 15 μm, the algae aggregates preferably having a characteristic size of less than about 200 μm.

Embodiment 4. The method of Embodiment 2 or Embodiment 3, wherein the algae have a first morphology and the algae aggregates have a second morphology.

Embodiment 5. The method of any one of Embodiments 2-4, wherein the algae aggregates further comprise at least one compound excreted by the algae.

Embodiment 6. The method of any of the previous embodiments, wherein the algae comprises at least 10 wt % of a first type of algae relative to the total weight of algae in the feed, and at least 10 wt % of a second type of algae relative to the total weight of algae in the feed.

Embodiment 7. The method of Embodiment 6, wherein the first type of algae has a first morphology, such as a cylindrical morphology, and the second type of algae has a second morphology, such as a spherical morphology.

Embodiment 8. The method of Embodiment 6 or Embodiment 7, wherein the algae aggregates have a morphology different from a morphology for a first type of algae and different from a morphology for a second type of algae.

Embodiment 9. The method of any of Embodiments 6-8, wherein a ratio of a characteristic length of a first type of algae and a characteristic length of a second type of algae is from about 1:3 to about 3:1.

Embodiment 10. The method of any of the above embodiments, wherein the filtration medium has a pore size of from about 1 µm to about 20 µm.

Embodiment 11. The method of any of the above embodiments, wherein the temperature during aging and filtration is from about 10° C. to about 40° C.

Embodiment 12. The method of any of the above embodiments, wherein the aging of the aqueous feed containing algae occurs in an environment that is deficient in at least one nutrient.

Embodiment 13. The method of Embodiment 12, wherein the at least one deficient nutrient is deficient based on being present in an amount below a threshold value for algae growth.

Embodiment 14. The method of Embodiment 12 or Embodiment 13, wherein the at least one deficient nutrient is $O_2$, $CO_2$, nitrogen, phosphorous, light energy, or a combination thereof.

Embodiment 15. The method of any of the above embodiments, wherein the aging and filtering are performed in the same vessel.

EXAMPLE 1

Algae Aggregation by Aging (*Cyclotella*)

~50 ml cultures of *Cyclotella* WT 293 (approximately 1 wt % algae in water) were placed in glass containers. Individual *Cyclotella* algae appeared to have a roughly cylindrical morphology with a characteristic length of about 4-5 µm. The containers were closed and allowed to age for ~24 hours, ~48 hours, and ~120 hours, respectively. During aging, the containers were maintained in a closed state in an unaerated environment, including no purging with air or $CO_2$. The temperature during aging was about 25° C. while the pressure during aging was about 15 psia or about 100 kPaa (roughly standard ambient pressure).

After aging for the indicated time periods, an opening at the bottom of the vessel was opened, and the algae cultures were passed through a filter at the bottom of the vessel under pressure. The filter corresponded to filter paper with a pore size of ~2.7 µm on top of an aluminum oxide frit with a pore size of ~20 µm. The pressure during filtration was about 500 psig (about 3.5 MPag), and the temperature was about 25° C. The filtration processes were characterized based on filtrate volume versus time and based on microscopy on the filter cake remaining on the filter paper after filtration.

One of the algae cultures was aged for ~24 hours and then filtered using the conditions noted above. After aging for ~24 hours, approximately 240 minutes were required to pass the ~50 ml of water through the filter. The filter cake remaining on the filter paper visually appeared to have a light tan color. Viewing the filter cake using a microscope with ~32× magnification showed little or no aggregation of the algae. A second algae culture was aged for ~48 hours and then filtered. After aging for ~48 hours, approximately 180 minutes were required to pass the ~50 ml of water through the filter. Thus, aging for ~48 hours provided only minimal improvement relative to aging for ~24 hours.

A third algae culture was aged for ~120 hours prior to filtration. After aging for ~120 hours, only about 20 minutes were required to pass the ~50 ml of water through the filter. The filter cake remaining on the filter paper visually appeared to have a darker greenish-brown color. Viewing the filter cake at ~32× magnification appeared to show aggregated algae structures with a crystalline appearance and an apparent crystal (particle) size of about 15 µm to about 200 µm. Due in part to the large size of the aggregated algae crystals (or quasi-crystals), a reduced amount of clogging was observed to occur for the pores of the filter paper, and the filter cake above the filter paper appeared to retain a higher permeability.

As an additional example, a similar filtration test was performed using *Cyclotella* 2272, which is another strain of *Cyclotella*. Similar enhancement of filtration rates was obtained after aging of ~120 hours.

EXAMPLE 2

Algae Aggregation by Aging (*Nannochloropsis*)

The procedures used in Example 1 were used to also study a ~50 ml sample of *Nannochloropsis* WT 35 algae. *Nannochloropsis* were observed to have a roughly spherical morphology with a characteristic length (diameter) of about 1 µm. Samples of *Nannochloropsis* were aged for ~24 hours and ~96 hours prior to filtration.

As described above, after aging for the indicated time periods, an opening at the bottom of the vessel was opened, and the algae cultures were passed through a filter at the bottom of the vessel under pressure. The filter corresponded to filter paper with a pore size of ~2.7 µm on top of an aluminum oxide frit with a pore size of ~20 µm. The pressure during filtration was about 500 psig (about 3.5 MPag), and the temperature was about 25° C. The filtration processes were characterized based on filtrate volume versus time and based on microscopy on the filter cake remaining on the filter paper after filtration.

One of the algae cultures was aged for ~24 hours and then filtered using the conditions noted above. The filtration process was stopped after about 210 minutes. After ~210 minutes, only ~4.5 ml of the water had passed through the filter and out of the vessel. The filter cake remaining on the filter paper visually appeared to have a light green color, with only portions of the filter appearing to show evidence of a filter cake. Viewing the filter cake using a microscope with ~32× magnification appeared to show little or no aggregation of the algae. Due to the small size of the individual *Nannochloropsis* algae (~1 µm spherical morphology), it is believed that the minimal amount of water that passed through the filter was due to clogging of the pores of the filter paper.

A second algae culture was aged for ~96 hours prior to filtration. After aging for ~96 hours, only about 8 minutes were required to pass the ~50 ml of water through the filter. The filter cake remaining on the filter paper visually appeared to have a darker green color. Additionally, viewing the filter cake at ~32× magnification appeared to show a still darker colored extracellular material between aggregated algae structures having an apparent crystal (particle) size of about 15 μm to about 200 μm. The relatively quick filtration of the full algae culture indicated that little or no clogging of the filter was observed. This was believed to be due in part to the relatively large aggregates that formed with the assistance of the extracellular material excreted by the *Nannochloropsis*. This example generally shows the applicability of the methods described herein for filtration of algae cultures.

EXAMPLE 3

Modeling of *Cyclotella* Filtration

The data obtained for *Cyclotella* WT 293 in Example 1 was also analyzed using the Hermans and Breede constant pressure filtration model. In this approach, the filtration was modeled from first principles of classical mechanics while taking into account two features of a filtration process that cause filter resistance. The modeled features included filter medium pore plugging and filter cake permeability.

FIG. 1 shows a plot of filter resistance versus time based on a fit of the filtration data in Example 1 to the Hermans and Breede model. As shown in FIG. 1, the filtration experiments after ~24 hours and ~48 hours of aging appeared to have a similar shape and appeared to asymptotically approach a similar filtration rate. This indicated a similar mechanism for filtration after the shorter aging times. By contrast, the filtration after ~120 hours of aging appeared to show qualitatively different behavior, indicating that aging the culture appeared to cause a fundamental change in the filtration process.

What is claimed is:

1. A method for harvesting algae, comprising:
    aging an aqueous feed containing algae in an unaerated environment for a period of at least about 90 hours; and
    filtering the aqueous feed through a filter medium at a pressure of about 25 psig (about 170 kPag) to about 1500 psig (about 10.3 MPag) to substantially separate the algae from the aqueous feed.

2. The method of claim 1, wherein the filtration medium has a pore size of from about 1 μm to about 20 μm.

3. The method of claim 1, wherein the temperature during aging and filtration is from about 10° C. to about 40° C.

4. The method of claim 1, wherein aging the aqueous feed containing algae further comprises aging the aqueous feed containing algae in an environment that is deficient in at least one nutrient.

5. The method of claim 4, wherein the at least one deficient nutrient is deficient based on being present in an amount below a threshold value for algae growth.

6. The method of claim 4, wherein the at least one deficient nutrient is $O_2$, $CO_2$, nitrogen, phosphorous, light energy, or a combination thereof.

7. The method of claim 1, wherein the aging and filtering are performed in the same vessel.

8. The method of claim 1, wherein the algae separated from the aqueous feed comprise algae aggregates.

9. The method of claim 8, wherein the algae have a characteristic size of about 10 μm or less and the algae aggregates have a characteristic size of at least about 15 μm.

10. The method of claim 8, wherein the algae have a first morphology and the algae aggregates have a second morphology.

11. The method of claim 8, wherein the algae aggregates further comprise at least one compound excreted by the algae.

12. A method for harvesting algae, comprising:
    aging an aqueous feed containing at least two types of algae in an unaerated environment for a period of at least about 90 hours, the algae comprising at least 10 wt % of each of the at least two types of algae relative to the total weight of algae in the feed; and
    filtering the aqueous feed through a filter medium at a pressure of about 25 psig (about 170 kPag) to about 1500 psig (about 10.3 MPag) to substantially separate the algae from the aqueous feed.

13. The method of claim 12, wherein the algae separated from the aqueous feed comprise algae aggregates having a characteristic size of about 15 μm to about 200 μm.

14. The method of claim 12, wherein a first type of algae has a cylindrical morphology and a second type of algae has a spherical morphology.

15. The method of claim 12, wherein the algae aggregates have a morphology different from a morphology for a first type of algae and different from a morphology for a second type of algae.

16. The method of claim 12, wherein a ratio of a characteristic length of a first type of algae and a characteristic length of a second type of algae is from about 1:3 to about 3:1.

17. The method of claim 12, wherein the aging and filtering are performed in the same vessel.

18. A method for harvesting algae, comprising:
    aging an aqueous feed containing algae in an unaerated environment for a period of at least about 90 hours, the algae comprising at least 10 wt % of a first type of algae relative to the total weight of algae in the feed, and at least 10 wt % of a second type of algae relative to the total weight of algae in the feed, the first type of algae having a first morphology and the second type of algae having a second morphology; and
    filtering the aqueous feed through a filter medium at a pressure of about 25 psig (about 170 kPag) to about 1500 psig (about 10.3 MPag) to substantially separate the algae from the aqueous feed.

19. The method of claim 18, wherein the first type of algae has a cylindrical morphology and the second type of algae has a spherical morphology.

20. The method of claim 18, wherein a ratio of a characteristic length of the at least first type of algae and a characteristic length of the at least second type of algae is from about 1:3 to about 3:1.

* * * * *